(12) United States Patent
Hayashi

(10) Patent No.: US 7,713,717 B2
(45) Date of Patent: May 11, 2010

(54) METHOD OF PREPARING YEAST FOR FERMENTATION TEST

(75) Inventor: Nobuyuki Hayashi, Tokyo (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 339 days.

(21) Appl. No.: 10/468,295

(22) PCT Filed: Feb. 18, 2002

(86) PCT No.: PCT/JP02/01365

§ 371 (c)(1),
(2), (4) Date: Aug. 19, 2003

(87) PCT Pub. No.: WO02/066673

PCT Pub. Date: Aug. 29, 2002

(65) Prior Publication Data

US 2004/0072329 A1   Apr. 15, 2004

(30) Foreign Application Priority Data

Feb. 19, 2001   (JP) ............................. 2001-042051

(51) Int. Cl.
| A23C 9/12 | (2006.01) |
| A23J 1/00 | (2006.01) |
| A23L 1/00 | (2006.01) |
| A23L 1/28 | (2006.01) |
| C12C 7/00 | (2006.01) |
| C12N 1/00 | (2006.01) |
| C12Q 1/02 | (2006.01) |
| C12C 3/12 | (2006.01) |

(52) U.S. Cl. .......................... 435/29; 426/29; 426/60; 426/62; 426/656; 435/254.2; 435/255.1

(58) Field of Classification Search ................. None
See application file for complete search history.

(56) References Cited

U.S. PATENT DOCUMENTS

| 2,803,546 A | * | 8/1957 | Bergmann et al. ............. 426/13 |
| 2,964,406 A | * | 12/1960 | Bockelmann et al. .......... 426/9 |
| 3,039,876 A | * | 6/1962 | Baker et al. .................... 426/13 |
| 3,373,040 A | * | 3/1968 | Gluek ........................... 426/13 |
| 3,711,292 A | * | 1/1973 | Sfat et al. ...................... 426/13 |
| 3,716,365 A | * | 2/1973 | Walmsley et al. ............. 426/29 |
| 3,717,471 A | * | 2/1973 | Sfat et al. ...................... 426/13 |
| 5,888,760 A | * | 3/1999 | Godsey et al. ................ 435/34 |
| 6,361,808 B1 | * | 3/2002 | Souppe et al. ................. 426/29 |
| 7,022,354 B1 | * | 4/2006 | Sato et al. ...................... 426/11 |
| 2004/0072329 A1 | * | 4/2004 | Hayashi ................. 435/254.21 |

FOREIGN PATENT DOCUMENTS

JP    63-216484 A    9/1998

OTHER PUBLICATIONS

Edited by K. Noshiro et al., "Jozo no Jiten", Kabushiki Kaisha Asakura Shoten, Nov. 10, 1988, pp. 260 to 261.
K. Krishna et al., "Drying/Kilning of Barley Malt", *Papers. American Society of Agricultural Engineers*, 1999, pp. 23p, paper No. 99-6024.

* cited by examiner

*Primary Examiner*—David M. Naff
*Assistant Examiner*—Deborah K. Ware
(74) *Attorney, Agent, or Firm*—Foley & Lardner LLP

(57) ABSTRACT

A method of preparing a yeast usable in a fermentation test for evaluating malt on the laboratory scale whereby more reproducible test data can be obtained regardless of the operation conditions of a plant, etc.; and a medium to be used therein. A yeast for the fermentation test for evaluating malt is prepared by culturing a yeast in a liquid medium containing 0 to 2.5% by weight of glucose, 6.0 to 9.0% by weight of maltose, 0 to 2.5% by weight of sorbitol, 0 to 1.0% by weight of peptone and 0.3 to 1.0% by weight of yeast extract at 10 to 20° C. for 2 to 4 days under shaking (primary culture), then in the medium in an increased amount compared with the primary culture at 10 to 20° C. for 3 or 4 days under shaking (secondary culture), then in the medium in a further increased amount compared with the secondary culture at 8 to 9° C. for 7 to 9 days under stirring until the plats attains 3.0° P. or less (tertiary culture), allowing to stand in a cold room for 3 to 24 hours and then collecting the yeast.

5 Claims, 3 Drawing Sheets

METHOD OF PREPARING YEAST FOR FERMENTATION TEST

TECHNICAL FIELD

The present invention relates to a method of preparing yeast usable to test the quality of malt used for beer brewing, and to a medium to be used in said method of preparing the yeast.

BACKGROUND ART

Malt used for beer brewing is an ingredient which has strong influence over the determination of the taste or flavor of beer, and it is also said to be the most important thing of beer. Malt contains various components such as protein, starch, extract and the like, and the composition of said components sometimes determines the quality of malt. However, it is said that the quality of fermentation of wort made from said malt is the most important factor which determines the quality of malt. Beer is generally produced by grinding malt, mashing, filtration and boiling to prepare wort, followed by adding yeast to the cooled wort to proceed fermentation. Therefore, if the quality of malt is good, the fermentation of yeast will proceed actively, and beer wherein the flavor is also excellent can be produced. However, if the quality of malt is not good, the fermentation will proceed only very slowly, and it is possible that beer with little commercial value is produced.

Moreover, in beer brewing, fermentation is proceeded in a condition wherein the wort in which yeast is suspended, is left at rest in a fermentation tank. However, the following ability is required for the yeast: to ferment in a condition wherein the yeast is diffused into wort, to precipitate when the fermentation is completed, and to ensure the amount of yeast necessary for the next fermentation. As for lager type beer, bottom fermentation yeast is generally used, and most of these yeasts have the ability to flocculate between yeasts. The flocculation of the bottom fermentation yeast is an extremely valuable characteristic for the brewer. That is a characteristic wherein the bottom fermentation yeast is dispersed by sugar in the wort, to make a block by flocculating each other when sugar disappears after fermentation, then to precipitate and to separate from the liquid. However, malt also comprises materials that promote flocculation of yeast, and depending on the crop situation of barley of that year, there is malt comprising many materials that promote flocculation of yeast and it sometimes happens that yeast in the wort is precipitated at an early stage of the fermentation. Said materials that promote flocculation, are generally called premature yeast flocculation factors, and it is important to know how many premature yeast flocculation factors are comprised in the malt, when managing fermentation.

Therefore, it is very important to know the quality of malt, especially the characteristics of fermentation, before using malt in beer brewing. Recently, by chemical analysis, it became possible to know the content of protein, starch, extract and the like, and to estimate on some level when the the yeast is fermented. However, in order to know how much extract will be converted to alcohol when fermentation is actually proceed, or how much the premature yeast flocculation factor will precipitate yeast, it is necessary to actually prepare wort from malt, and to proceed fermentation. Therefore, the present inventors have reported a method of mashing malt or a method of fermentation test of a small scale to evaluate the quality of malt, especially the characteristics of fermentation, on a laboratory scale before the actual brewing, as a method of a fermentation test for evaluating malt (EUROPEAN BREWERY CONVENTION MONOGRAPH XXIII E.B.C.-SYMPOSIUM MALTING TECHNOLOGY ANDERNACH•GERMANY NOVEMBER 1994, 110-136). This method of fermentation test for evaluating malt has been established as a standard analysis, after many researchers have considered various aspects such as method of selecting malt used as control (called control malt), determination of control for mashing temperature, method of handling yeast and the like. By incorporating the results of chemical and physical analysis and the like to the results of this fermentation test for evaluating malt, a comprehensive decision is made, and the results are used as criterion when purchasing malt from a manufacturer.

The summary of the above-mentioned fermentation test for evaluating malt is explained in detail as follows: first, as for the process of grinding malt, the grinding scale of the disk mill is adjusted so that the intervals between disks are precisely 1.00 mm, 300 g of malt is ground with the disk mill, and the total amount is put in a 2 L mashing beaker (stainless-steel beaker). 1.8 L of tap water of 46 to 47° C. is added to the mashing beaker comprising the ground malt, the mixture is put into a large mash tun which the water temperature is adjusted to 45° C., and by continuing to stir, the mixture is mashed at a course of temperature according to the Congress method (45° C., 30 minutes→ raise temperature 1° C. every minute→70° C., 1 hour). When mashing is completed, the mash is filtered with a conical filtration cloth, and the filtration speed is determined. The amount of the wort which filtration is completed and the plato (° P.) are determined. 1.2 L of said wort is put in a 2 L conical flask, 2.6 g of fresh hop is added, the opening of the conical flask is covered with a funnel, and by boiling the mixture for 1 hour, the bubbling of the surface is examined. After boiling, the condition of Bruch and the clarity are examined. The boiled wort is cooled to around 50° C., filtered with Toyo filter paper No.2 (diameter 30 cm), then the filtrate is left overnight at around 8° C., filtered with Toyo filter paper No.2 to remove cold breaks, and then tap water is added to adjust the plato of wort to 11.0° P. The wort obtained which has been boiled is used in the fermentation test.

Approximately 500 ml of yeast in a form of mud collected from the fermentation tunk is put in a 1 L beaker, an equal amount of cold water is added, stirred well, and when the yeast is precipitated, the supernatant is thrown away. This operation is repeated for 4 times or more, and the liquid is filtered with a 100 mesh wire net. By using a Buechner funnel with a Toyo filter paper No.7 attached to it, yeast suspended solution is filtered by aspiration to obtain pressed yeast. 500 ml of said wort which has been boiled, and 1.75 g of pressed yeast are added to a 1 L flask for fermentation test, the mixture is shaken 30 times to disperse the yeast, and is left at rest for 2 hours at a constant temperature (20° C.±1° C.). Yeast-added wort thus obtained is moved to a KI fermentation tube (capacity of 500 ml, diameter 25 mm, height 1250 mm) and is left at rest at 8° C.±0.2° C. for 7 days. As control, control malt is used. OD 800, plato, AAL (apparent attenuation limit), and premature flocculating nature of yeast are determined for 1 to 8 days, compared with the control, and the fermentation characteristics of the test malt are evaluated.

The above-mentioned fermentation test for evaluating malt is an excellent method that has been established as a standard analysis to evaluate the fermentation characteristics of malt. However, during the process of considering the method in order to obtain more reproducible test results, it was found that the physiological condition of yeast to be used could possibly be a factor having influence over the test results. That is, the fermentation test for evaluating malt is a kind of bioassay by a yeast. Generally, yeast collected after actually being used in a beer plant (plant yeast) is used in the above fermentation test for evaluating malt, but in a beer plant, as there are busy season, off season or manufacture discontinuation due to maintenance and repairing, not only it is hard to collect yeast in the same physiological condition at all times, but also the fermentation activity of the yeast may change depending on the storage condition or transportation condition of the yeast. Moreover, in case a malt manufacturer conduct independently a fermentation test for evaluating malt or a beer manufacturer outsource a fermentation test for evaluating malt and the like, it is not always possible to use yeast collected from a beer plant in the same condition. Thus, it was estimated that there were problems for the reproducibility of the test results. The object of the present invention is to provide a method of preparing yeast usable in a fermentation test for evaluating malt on a laboratory scale, in order to obtain more reproducible test results, without being influenced by the operating conditions of the plant or the like, and a medium to be used therein.

DISCLOSURE OF THE INVENTION

The present inventors have made a keen study to solve the above-mentioned problems, and have found out that as for a fermentation test for evaluating malt on a laboratory scale, more reproducible test results could be obtained: by controlling the multiplication of the yeast used by making the apparent extract an indicator; by always using yeast in the same physiological condition in a fermentation test for evaluating malt; and by using a liquid medium containing 6 to 12% by weight of sugar in which yeast can ferment and a total amount of 1400 to 3000 mg/L of free amino acid as the medium to be used. The present invention has been thus completed.

In other words, the present invention relates to a method of preparing yeast usable in a fermentation test for evaluating malt, wherein a liquid medium containing 6 to 12% by weight of sugar in which yeast can ferment and a total amount of 1400 to 3000 mg/L of free amino acid as compound ingredients is used to shake and culture the yeast until the plato becomes 3.0° P. or less, and then the yeast is collected (claim 1); a method of preparing yeast usable in a fermentation test for evaluating malt, wherein a liquid medium containing 6 to 12% by weight of sugar in which yeast can ferment and a total amount of 1400 to 3000 mg/L of free amino acid is used to shake and culture at 10 to 20° C. for 2 to 4 days (primary culture), the amount of medium is increased more than the primary culture to shake and culture at 10 to 20° C. for 3 to 4 days (secondary culture), the amount of medium is increased more than the secondary culture to stir and culture at 8 to 9° C. for 7 to 9 days (tertiary culture), then allowed to stand in a cold room, and then the yeast is collected (claim 2); the method of preparing yeast usable in a fermentation test for evaluating malt according to claim 1 or 2, wherein a liquid medium containing 0 to 2.5% by weight of glucose, 6.0 to 9.0% by weight of maltose, 0 to 2.5% by weight of sorbitol, 0 to 1.0% by weight of peptone and 0.3 to 1.0% by weight of yeast extract, is used as the liquid medium containing 6 to 12% by weight of sugar in which yeast can ferment and a total amount of 1400 to 3000 mg/L of free amino acid (claim 3); the method of preparing yeast usable in a fermentation test for evaluating malt according to claim 3, wherein a liquid medium containing 1.5% by weight of glucose, 6.5% by weight of maltose, 2.0% by weight of sorbitol, 0.2% by weight of peptone and 0.4% by weight of yeast extract is used as the liquid medium containing 6 to 12% by weight of sugar in which yeast can ferment and a total amount of 1400 to 3000 mg/L of free amino acid (claim 4); and the method of preparing yeast usable in a fermentation test for evaluating malt according to any of claims 2 to 4, wherein the tertiary culture is proceeded by adding the secondary culture solution to 4 L of liquid medium so that the amount of yeast cells becomes $1.0 \times 10^{10}$ to $1.2 \times 10^{10}$ cells (claim 5).

Furthermore, the present invention relates to a medium used for preparing yeast in a fermentation test for evaluating malt, wherein the medium contains 0 to 2.5% by weight of glucose, 6.0 to 9.0% by weight of maltose, 0 to 2.5% by weight of sorbitol, 0 to 1.0% by weight of peptone and 0.3 to 1.0% by weight of yeast extract (claim 6); and the medium for preparing yeast in a fermentation test for evaluating malt according to claim 6, wherein the medium contains 1.5% by weight of glucose, 6.5% by weight of maltose, 2.0% by weight of sorbitol, 0.2% by weight of peptone and 0.4% by weight of yeast extract (claim 7).

BEST MODE OF CARRYING OUT THE INVENTION

Figure 1:
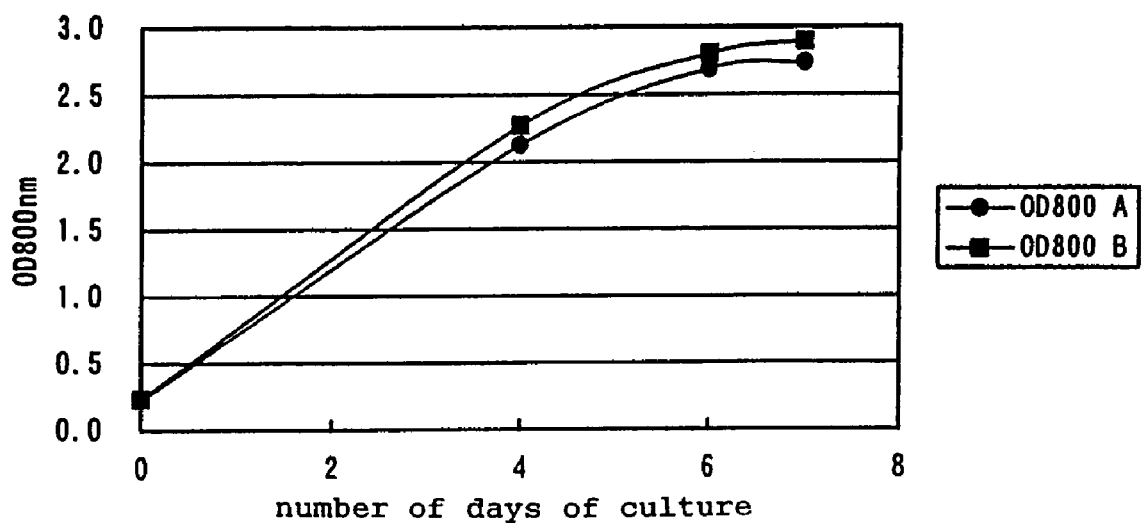
FIG. 1 shows the results obtained by determining the process of culture of the tertiary culture at OD value (OD 800 nm) where the wavelength is 800 nm.

As a method of preparing yeast usable in a fermentation test for evaluating malt according to the present invention, there is no specific limitation as long as it is a method wherein a liquid medium containing 6 to 12% by weight of sugar in which yeast can ferment and a total amount of 1400 to 3000 mg/L of free amino acid as compound ingredients is used to shake and culture the yeast until the plato becomes 3.0° P. or less, and then the yeast is collected; or a method wherein a liquid medium containing 6 to 12% by weight of sugar in which yeast can ferment and a total amount of 1400 to 3000 mg/L of free amino acid is used to shake and culture at 10 to 20° C. for 2 to 4 days (primary culture), the amount of medium is increased more than the primary culture to shake and culture at 10 to 20° C. for 3 to 4 days (secondary culture), the amount of medium is increased more than the secondary culture to stir and culture at 8 to 9° C. for 7 to 9 days (tertiary culture), then allowed to stand in a cold room for 3 to 24 hours and then the precipitated yeast is collected. For example, as for the above-mentioned fermentation test for evaluating malt, the method of fermentation test for evaluating malt reported by the present inventors (EUROPEAN BREWERY CONVENTION MONOGRAPH XXIII E.B.C.-SYMPOSIUM MALTING TECHNOLOGY ANDERNACH• GERMANY NOVEMBER 1994, 110-136) can be used.

As initial cultures usable in the above-mentioned primary culture, yeast which has been slant cultured on a normal malt agar medium can be used, and said slant cultured yeast can be used for about 6 months if stored at 4° C. To ensure the amount of yeast collected, it is preferable that tertiary culture is proceeded by adding the secondary culture solution to 4 L of liquid medium so that the amount of yeast cells becomes $1.0 \times 10^{10}$ to $1.2 \times 10^{10}$ cells.

Examples of the above-mentioned sugar in which yeast can ferment, include glucose, maltose, sucrose, fructose and the like, and sugar comprising glucose and maltose are preferable. Moreover, 6 to 12% by weight of said sugar, preferably 8 to 12% by weight is added. Additionally, specific examples of the above-mentioned materials comprising a total amount of 1400 to 3000 mg/L of free amino acid include peptone or yeast extract, but are not limited to these. Furthermore, the total amount of free amino acid can be obtained by a common procedure, using an amino acid analyzer. The total amount of free amino acid mentioned here refers to the total amount of: free aspartic acid, threonine, serine, glutamic acid, proline (imino acid), glycine, alanine, cystine, valine, methionine, isoleucine, leucine, tyrosine, phenylalanine, tryptophan, lysine, histidine, and arginine. Additionally, as a liquid medium containing 6 to 12% by weight of sugar in which yeast can ferment and a total amount of 1400 to 3000 mg/L of free amino acid, a liquid medium containing 0 to 2.5% by weight of glucose, 6.0 to 9.0% by weight of maltose, 0 to 2.5% by weight of sorbitol, 0 to 1.0% by weight of peptone and 0.3 to 1.0% by weight of yeast extract is preferable, and a liquid medium (HB medium) containing 1.5% by weight of glucose, 6.5% by weight of maltose, 2.0% by weight of sorbitol, 0.2% by weight of peptone and 0.4% by weight of yeast extract is especially preferable.

The present invention will be described further in detail by the following examples, while the technical scope of the present invention will not be limited to these examples. In addition, "%" refers to % by weight unless otherwise noticed.

EXAMPLE 1

Determination of Various Conditions for Culturing Yeast

To establish a method of preparing yeast for evaluating the fermentation characteristics of malt, culture condition of yeast was first considered. As the medium used when considering the culture condition, a YM medium [glucose 1%, peptone 0.5%, malt extract 0.3%, yeast extract 0.3%] and the like, which is generally used to culture yeast were taken as reference, and o medium [glucose 2.5%, maltose 7.5%, peptone 0.5%, yeast extract 0.3%; pH 6.2], prepared so that the plato is close to wort, was used. 1 platinum loop of yeast cultured in a malt agar medium was inoculated upon 8 ml of the above-mentioned 0 medium in the test tube to shake and culture at 14° C. for 2 to 4 days (primary culture). Total amount of culture of the primary culture was added to 150 ml of said 0 medium in a 300 ml conical flask to shake and culture at 14° C. for 3 to 4 days (secondary culture). Approximately $1.1 \times 10^{10}$ cells of yeast, obtained by the secondary culture, was added to 4 L of said 0 medium in a 5 L glass bottle to culture while stirring (250 rpm) at 9° C. for 7 to 9 days with a stirrer (tertiary culture).

To always provide yeast in the same physiological condition for malt fermentation, it is necessary to control the multiplication of yeast with some sort of indicator, and it was first considered if optical density (OD) being widely used to determine yeast concentration of a culture solution, was appropriate as an indicator. The results of the process of culture of the tertiary culture determined at OD value (OD 800 nm) when the wavelength is 800 nm are shown in FIG. 1. As it is also shown in FIG. 1, the multiplication of yeast could be confirmed by the increase of OD value. However, although being the same machine of the same manufacturer, when a different spectrophotometer (A, B) is used, there is a slight difference between the values. As to optical density, the position of the cuvette, the intensity of light source or the like differs according to the manufacturer or the type of machine, therefore, it is hard to say that the optical density is an absolute value. There is no problem if the same machine is always used when conducting experiments, but to obtain more reproducible test results, including in overseas research faculties, it was found that it is difficult to control the multiplication of yeast only with OD value.

Plato (° P.) is also widely used as a management indicator for yeast fermentation, and plato calculated from the gravity of the fermentation solution itself is called apparent extract (grade of apparent plato). As alcohol is generated when the fermentation proceeds, the apparent extract does not reflect exactly the remaining plato, but the value of the apparent extract can be easily determined by using a hydrometer or an oscillating-type density meter. Thus, it was considered if the apparent extract was effective as a management indicator for multiplication. The results of determining the relation between the number of days of culture of tertiary culture and the plato are shown in Table 1. From Table 1, it was found that about 7 days after the culture, the multiplication of yeast nearly turns to a stationary phase, and the amount of yeast collected gets close to the maximum value. However, in a fermentation test for evaluating malt, approximately 2 g of yeast cell is necessary per 1 sample, therefore, to treat more than 20 samples at once, the amount of yeast collected at one time should be more than 50 g. As for the case of 6 days after the culture and apparent extract being more than 3° P., there is no room for the amount required, and it was found that apparent extract should be 3° P. or less as for the management standard to decide the completion of the tertiary culture. Moreover, it was also found that the indication for the period of culture should be 7 days or more.

TABLE 1

| | Number of days of tertiary culture | | |
|---|---|---|---|
| | 6 days | 7 days | 8 days |
| Apparent extract (° P) | 3.73 | 1.68 | −0.21 |
| OD 800 nm | 2.77 | 2.91 | 3.19 |
| Amount of yeast collected (g) | 53 | 70 | 74 |

When the secondary culture is completed, yeast in the culture solution is added to the medium for the tertiary culture, to continue the culture. As it was estimated that the multiplication of yeast could be influenced by this added amount of yeast cells, the amount inoculated upon the tertiary culture was reduced, and then the amount of yeast multiplied, the amount of yeast collected and the like were determined at 7 days after the culture. The results are shown in Table 2. As it is shown in Table 2, it was found that when the amount of yeast inoculated is reduced, the apparent extract (° P.) increases little by little and OD 800 nm and the amount of yeast collected (g) decreases little by little. In order to surely reach the stationary phase at 7 days after the culture and to ensure the amount of yeast collected, it was found that the amount of inoculated cells should be around $1.0 \times 10^{10}$ cells ($\pm 0.1 \times 10^{10}$ cells).

TABLE 2

| | Amount inoculated upon the tertiary culture | | |
|---|---|---|---|
| | $1.1 \times 10^{10}$ cells | $6.4 \times 10^9$ cells | $4.1 \times 10^9$ cells |
| Apparent extract (° P) | 2.16 | 2.62 | 3.19 |
| OD 800 nm | 2.99 | 2.85 | 2.89 |
| Amount of yeast collected (g) | 65.8 | 51.7 | 49.2 |

EXAMPLE 2

Consideration of Medium for Culturing Yeast

Under the culture condition as determined above, the influence of the composition of the medium used for culturing yeast to the malt evaluation was examined. Considering that wort is prepared to conduct a fermentation test for evaluating malt, it was estimated that it would be beneficial to use a medium with a composition close to wort, also in the culture of the precedent stage, O medium was prepared as described previously. The tertiary culture in 4 L of O medium in a 5L glass bottle, was also conducted in wort at the same time as the culture in O medium. Then, the carbon source, composition of nitrogen source, and their consumption were compared. The results are shown in Table 3. From Table 3, it could be seen that the sugar composition of O medium slightly differs compared to wort, and also that the amount of amino acid consumed after the culture is larger compared to wort. Therefore, as a medium wherein these points are adjusted and improved, HB medium [glucose 1.5%, maltose 6.5%, sorbitol 2.0%, peptone 0.2%, yeast extract 0.4%; pH 5.6] was prepared. By conducting the culture in the same manner, it was found that the sugar composition and the amount of nitrogen consumed became close to wort.

TABLE 3

| | Wort | | O medium | | HB medium | |
|---|---|---|---|---|---|---|
| | Before culture | After culture | Before culture | After culture | Before culture | After culture |
| Glucose (%) | 1.2 | 0.0 | 2.5 | 0.0 | 1.5 | 0.0 |
| Maltose (%) | 5.6 | 0.2 | 7.5 | 2.1 | 6.5 | 0.2 |
| Total nitrogen (mg/100 ml) | 88.9 | 54.4 (34.5) | 101.6 | 80.7 (20.9) | 75.4 | 45.4 (30.0) |
| Total free amino acid(mg/l) | 1924 | 426 (1498) | 1693 | 82 (1611) | 1547 | 57 (1490) |
| Apparent extract (° P) | 11.03 | 1.90 | 10.45 | 1.53 | 10.17 | 1.04 |
| Amount of yeast collected (g) | — | 59.2 | — | 60.3 | — | 70.0 |

The numbers in parenthesis show the amount consumed.

EXAMPLE 3

Fermentation Test for Evaluating Malt

Figure 2:
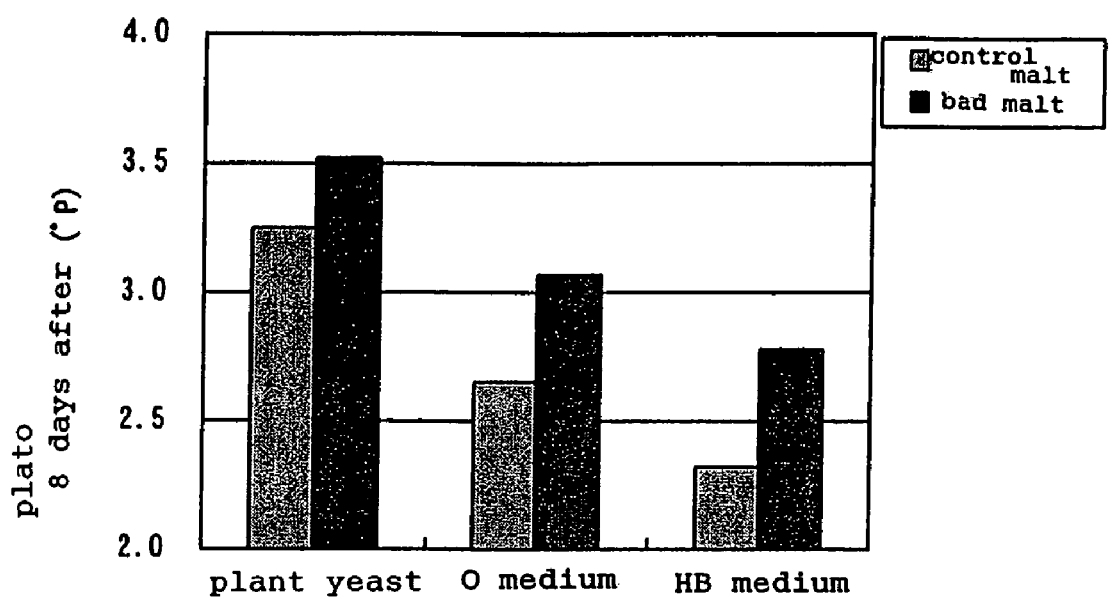
FIG. 2 shows the results of the fermentation test for evaluating malt of the present invention, regarding plant yeast, yeast prepared in O medium and yeast prepared in HB medium, by using control malt and bad malt.
Figure 2:
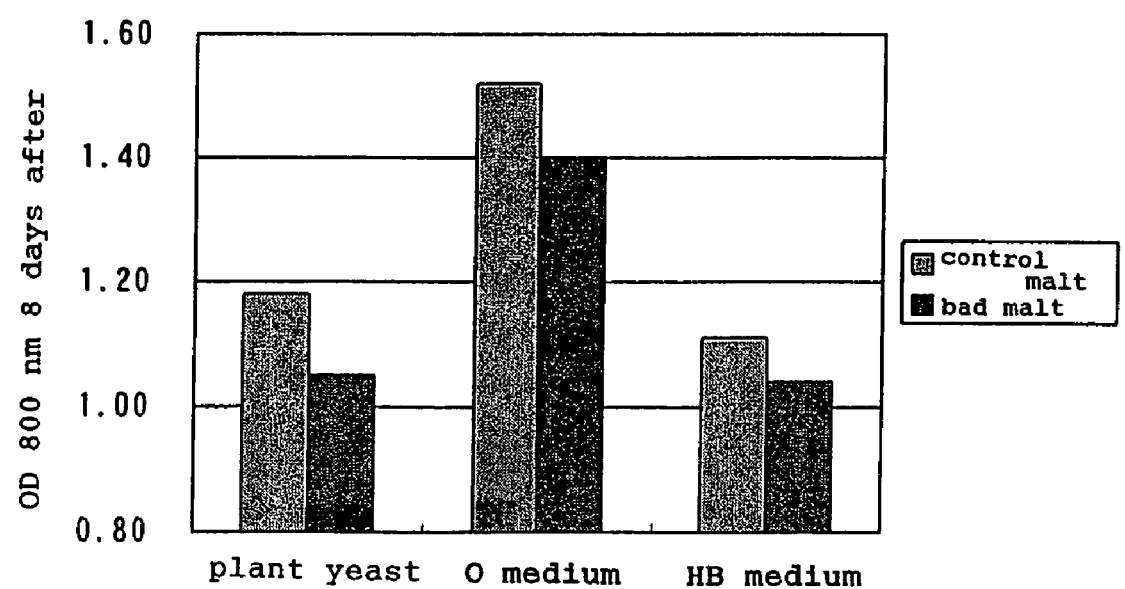
Figure 3:
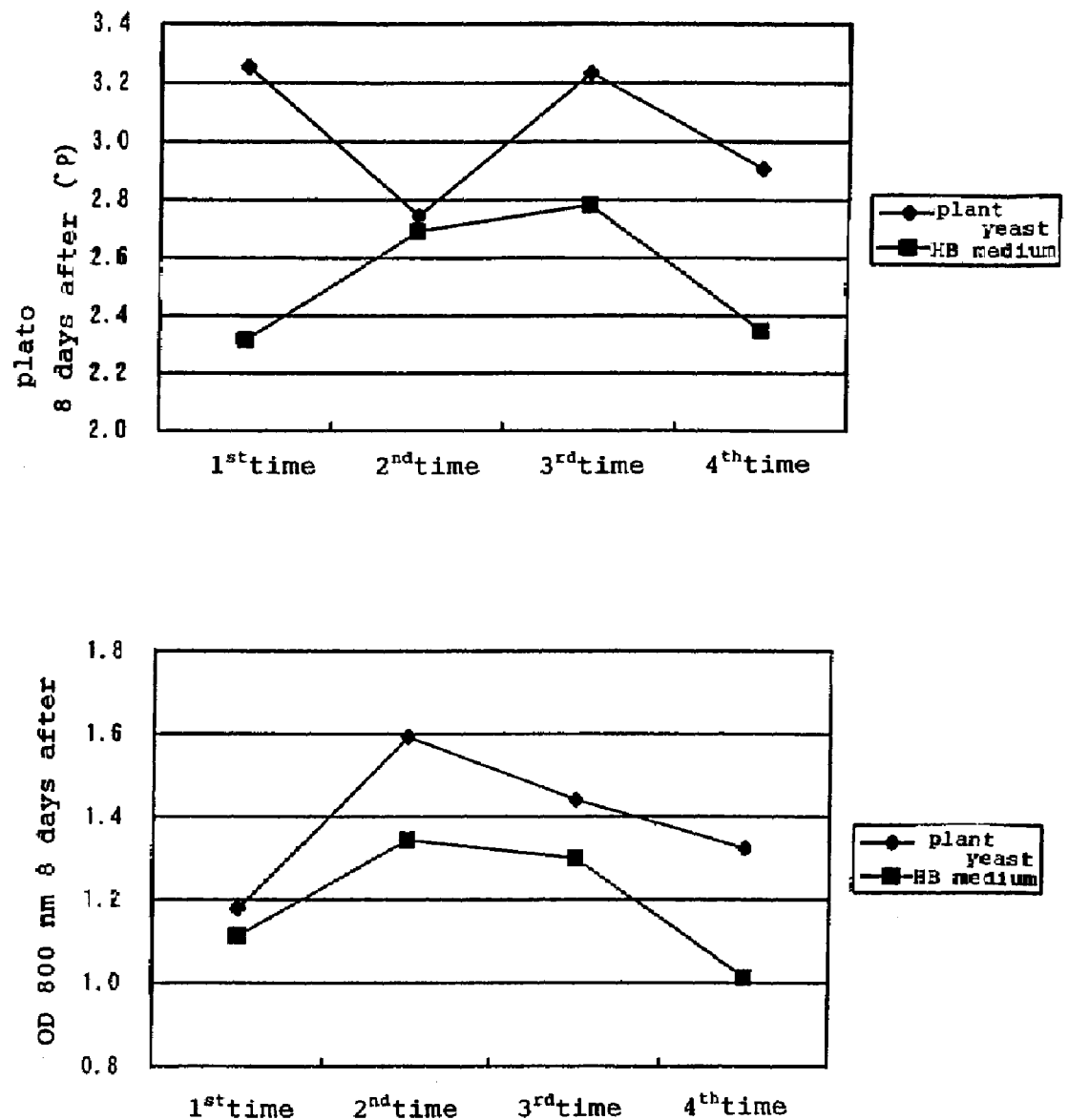
FIG. 3 shows the results of the fermentation test for evaluating malt of the present invention repeated 4 times, with the use of plant yeast and yeast prepared in HB medium.

By using yeast usable in a fermentation test for evaluating malt prepared in the above-mentioned HB medium and O medium, the fermentation test for evaluating malt was actually conducted. As control, plant yeast that is used conventionally was used without change. As for the method of the fermentation test for evaluating malt, it was conducted according to the method described in the previous report (EUROPEAN BREWERY CONVENTION MONOGRAPH XXIII E.B.C.-SYMPOSIUM MALTING TECHNOLOGY ANDERNACH GERMANY NOVEMBER 1994, 110-136). As a test malt, a control malt having good fermentation characteristics used as control in ordinary experiment, and a bad malt known beforehand to have inferior fermentation characteristics were used. Therefore, as characteristics of yeast suitable for a fermentation test for evaluating malt, it is preferable that the sugar consumption is active with wort made from control malt, and that the sugar consumption and the amount of floating yeast with the bad malt is clearly different from the control malt. The fermentation test for evaluating malt was conducted regarding plant yeast, yeast prepared in O medium and yeast prepared in HB medium, by using control malt and bad malt. The results of the plato (° P.) and OD 800 nm at 8 days after the fermentation test for evaluating malt are shown in FIG. 2. From these results, it was found that the sugar consumption for yeast prepared in HB medium was best, and the sugar consumption of wort made from bad malt was not good compared with wort made from control malt and that they were clearly different. It was also confirmed that for the optical density, although sugar was not completely consumed in bad malt, there were only a few suspended yeast in each case. Next, by using plant yeast and yeast prepared in HB medium, the double-fermentation test for evaluating malt was conducted 4 times repeatedly. The results are shown in FIG. 3. As it is shown in FIG. 3, for the yeast prepared in HB medium, the plato at 8 days after the fermentation test was stable and less than 3° P., and the total dispersion of the plato at 8 days after the fermentation test was lower than the plant yeast (variance of plant yeast: 0.14, variance of HB medium: 0.08). Thus, according to the fermentation test for evaluating malt of the present invention, it was found that more reproducible results could be obtained.

As described above, it was found that HB medium or O medium, especially HB medium was effective as a medium for culturing yeast usable in a fermentation test for evaluating malt, and some mediums beside HB medium and O medium were prepared by changing the composition of the medium, said mediums were used to prepare yeast usable in a fermentation test for evaluating malt, and the fermentation test for evaluating malt was conducted. The results are shown in Table 4. HC medium, HD medium, HE medium and HF medium shown in Table 4 were found to be effective just like HB medium, as a medium for culturing yeast usable in a fermentation test for evaluating malt.

TABLE 4

| | HB medium | | HC medium | | HD medium | | HE medium | | HF medium | |
|---|---|---|---|---|---|---|---|---|---|---|
| Composition of medium | glucose | 1.5% | glucose | 2.0% | glucose | 2.5% | glucose | 1.5% | glucose | 0.5% |
| | maltose | 6.5% | maltose | 7.5% | maltose | 9.0% | maltose | 6.5% | maltose | 6.5% |
| | sorbitol | 2.0% | sorbitol | 2.5% | sorbitol | 2.5% | sorbitol | 2.0% | sorbitol | 2.0% |
| | peptone | 0.2% | peptone | 0.24% | peptone | 0.28% | peptone | 0.1% | peptone | 1.0% |
| | YE | 0.4% | YE | 0.48% | YE | 0.56% | YE | 0.2% | YE | 0.6% |
| Total nitrogen (mg/100 ml) | 77.4(35.0) | | 92.6(37.9) | | 107.1(38.5) | | 39.5(16.4) | | 239.9(49.2) | |
| Total free amino acid(mg/l) | 1650(1595) | | 1902(1836) | | 2235(2124) | | 819(797) | | 3274(2479) | |
| Amount of yeast collected (g) | 60.3 | | 65.5 | | 73 | | 30.1 | | 92.8 | |
| Fermentation test result | control malt | bad malt | control malt | bad malt | control malt | bad malt | control malt | bad malt | control malt | bad malt |
| Plato at 8 days after fermentation test | 2.47 | 3.67 | 2.44 | 3.41 | 2.34 | 3.17 | 2.42 | 3.13 | 2.46 | 3.62 |
| OD at 8 days after fermentation test | 1.02 | 0.94 | 0.92 | 0.78 | 0.91 | 0.80 | 0.89 | 0.61 | 1.08 | 0.89 |

YE: Yeast extract, numbers in parenthesis show the amount consumed after culture.

INDUSTRIAL APPLICABILITY

According to the present invention, more reproducible test results can be obtained without being influenced by the operating conditions of the plant and the like, in a fermentation test for evaluating malt which can evaluate on a laboratory scale, the level of premature flocculation factors comprised in malt, by using yeast wherein the physiological condition is more stable.

The invention claimed is:

1. A testing method using a yeast for evaluating fermentation characteristics of malt to be used in brewing beer, capable of obtaining a reproducible test result, the method comprising:
    (i) preparing yeast for use in the testing by culturing and shaking the yeast in a liquid medium comprising 6 to 12% by weight of sugar in which yeast can ferment, 1400 to 3000 mg/L of free amino acids until the resulting ferment reaches a plato of 3.0° P or less and collecting yeast from the ferment,
    (ii) producing a filtered wort by hot water filtration from a sample of a malt being evaluated for fermentation characteristics to be used in brewing beer, wherein the filtered wort is prepared by a grinding step in which the sample of malt is ground to form a ground malt, followed by a hot water filtration step in which the ground malt is added to hot water and filtered to obtain the filtered wort,
    (iii) adding the yeast collected above in step (i) to the filtered wort prepared from the sample of the malt in step (ii) to perform a fermentation test for estimating the fermentation characteristics of the malt sample,
    (iv) culturing the yeast in the wort in a flask to produce a yeast fermentation solution, and
    (v) evaluating the fermentation characteristics of the sample of the malt by measuring optical density at 800 nanometers (OD800), degrees plato, apparent attenuation limit and premature flocculating nature of the yeast fermentation solution.

2. The testing method according to claim 1, wherein preparing the yeast for use in the test is carried out by
    (i) culturing and shaking the yeast in the liquid medium containing 6 to 12% by weight sugar and 1400 to 3000 mg/L of free amino acids at 10 to 20 C for 2 to 4 days to form a primary yeast culture,
    (ii) culturing and shaking the primary yeast culture in additional liquid medium at 10 to 20° C. for 3 to 4 days to form a secondary yeast culture,
    (iii) culturing and shaking the secondary yeast culture in additional liquid medium at 8 to 9° C. for 7 to 9 days to form a tertiary yeast culture,
    (iv) allowing the tertiary culture to stand in a cold room, and
    (v) collecting the yeast from the tertiary culture.

3. The testing method according to claim 1, wherein the liquid medium containing 6 to 12% by weight sugar and 1400 to 3000 mg/L of free amino acids comprises 0 to 2.5% by weight of glucose, 6.0 to 9.0% by weight of maltose, 0 to 2.5% by weight of sorbitol, 0 to 1.0% by weight of peptone and 0.3 to 1.0% by weight of yeast extract.

4. The testing method according to claim 3, wherein the liquid medium containing 6 to 12% by weight sugar and 1400 to 3000 mg/L of free amino acids comprises 1.5% by weight of glucose, 6.5% by weight of maltose, 2.0% by weight of sorbitol, 0.2% by weight of peptone and 0.4% by weight of yeast extract.

5. The testing method according to claim 2, wherein the tertiary yeast culture is formed by adding a volume of the secondary yeast culture to 4 L of the liquid medium so that the amount of yeast cells in the liquid medium is $1.0 \times 10^{10}$ to $1.2 \times 10^{10}$ cells.

* * * * *